US009289380B2

(12) United States Patent
Blakely et al.

(10) Patent No.: US 9,289,380 B2
(45) Date of Patent: Mar. 22, 2016

(54) LONG ACTING PARASITICIDAL COMPOSITION CONTAINING A SALICYLANILIDE COMPOUND, A POLYMERIC SPECIES AND AT LEAST ONE OTHER ANTI-PARASITIC COMPOUND

(75) Inventors: William Blakely, Newry (GB); Lillian Cromie, Newry (GB); Sean Duffy, Newry (GB)

(73) Assignee: Norbrook Laboratories Limited, Newry (GB)

( * ) Notice: Subject to any disclaimer, the term of this patent is extended or adjusted under 35 U.S.C. 154(b) by 1720 days.

(21) Appl. No.: 10/504,331

(22) PCT Filed: Feb. 12, 2003

(86) PCT No.: PCT/GB03/00645
§ 371 (c)(1),
(2), (4) Date: Feb. 4, 2005

(87) PCT Pub. No.: WO03/072113
PCT Pub. Date: Sep. 4, 2003

(65) Prior Publication Data
US 2005/0118221 A1    Jun. 2, 2005

(30) Foreign Application Priority Data
Feb. 28, 2002  (GB) .................................. 0204712.4

(51) Int. Cl.
| A61K 31/167 | (2006.01) |
| A61K 9/00 | (2006.01) |
| A61K 31/277 | (2006.01) |
| A61K 31/7048 | (2006.01) |
| A61K 45/06 | (2006.01) |
| A61K 47/10 | (2006.01) |
| A61K 47/32 | (2006.01) |

(52) U.S. Cl.
CPC .............. *A61K 9/0019* (2013.01); *A61K 31/167* (2013.01); *A61K 31/277* (2013.01); *A61K 31/7048* (2013.01); *A61K 45/06* (2013.01); *A61K 47/10* (2013.01); *A61K 47/32* (2013.01)

(58) Field of Classification Search
CPC ............ A61K 2300/00; A61K 31/167; A61K 31/277; A61K 31/7048; A61K 45/06; A61K 47/10; A61K 47/32; A61K 9/0019
See application file for complete search history.

(56) References Cited

U.S. PATENT DOCUMENTS

| 3,950,360 A | 4/1976 | Aoki et al. |
| 4,005,218 A | 1/1977 | Janssen et al. |
| 4,128,632 A | 12/1978 | Lo et al. |
| 4,171,314 A | 10/1979 | Chabala et al. |
| 4,173,571 A | 11/1979 | Chabala et al. |
| 4,199,569 A | 4/1980 | Chabala et al. |
| 4,206,205 A | 6/1980 | Mrozik et al. |
| 4,310,519 A | 1/1982 | Albers-Schonberg et al. |
| 4,997,651 A * | 3/1991 | Poole et al. ................... 514/564 |
| 5,275,805 A | 1/1994 | Nabi et al. |
| 5,516,761 A | 5/1996 | Choi et al. |
| 5,773,422 A * | 6/1998 | Komer ........................... 514/30 |
| 6,193,989 B1 | 2/2001 | Lamberti |

FOREIGN PATENT DOCUMENTS

| DE | 2263509 | 7/1974 | |
| EP | 0 045 655 | 3/1985 | |
| EP | 0 146 414 | 10/1989 | |
| EP | 0 628 302 | 12/1994 | |
| FR | 2 739 778 | 4/1997 | |
| GB | 2213722 | 8/1989 | |
| WO | WO 94/28887 | 12/1994 | |
| WO | WO 95/05812 | 3/1995 | |
| WO | WO 9505812 A1 * | 3/1995 | ............. A61K 31/16 |
| WO | WO 95/16447 | 6/1995 | |
| WO | WO 00/61068 | 10/2000 | |
| WO | WO 01/60380 | 8/2001 | |
| WO | WO 02/09764 | 2/2002 | |
| WO | WO 02/094221 | 11/2002 | |

OTHER PUBLICATIONS

Swan, 1999, 70(2): 61-70.*
Riviere et al., Veterinary Pharmacology and Therapeutics, 2009, 1 page (1106).*
J. C. Chabala, "Ivermectin, a new broad-spectrum antiparasitic agent," *J. Med. Chem.* 23,1134 (1980) (Abstract only).
J. R. Egerton et al, "22, 23-Dihydroavermectin $B_1$, A New Broad-Spectrum Antiparasitic Agent," 136 *Brit. Vet. J.* 88-97 (1980).
W. C. Campbell et al, "Ivermectin: A Potent New Antiparasitic Agent," 221 *Science* 823-828 (1983).
J. Guerrero et al, "Anthelmintic Activity of Closantel Against *Ancylostoma caninum* in Dogs," 68 *J. Parasitol.* 616-619 (1983).
H. Van den Bossche et al, "Closantel, A New Antiparasitic Hydrogen Ionophore," 87 *Arch. Int. Physiol. Biochim*, 851-853 (1979).
H. J. Kane et al, "Metabolic Studies on the New Fasciolicidal Drug, Closantel," 1 *Mol. Biochem.Parasitol.* 347-355 (1980).

* cited by examiner

*Primary Examiner* — Kyle Purdy
(74) *Attorney, Agent, or Firm* — Porzio, Bromberg & Newman P.C.

(57) ABSTRACT

A composition prepared for treating animals suffering from parasites which parasites are known to be susceptible to at least one of the avermectins, milbemycins or salicylanilides, comprises for example ivermectin in an amount of from 0.1 to 10%(w/v), a solvent selected from the group consisting of glycerol formal, propylene glycol, polyethylene glycol and combinations thereof, and a salicylanilide such as closantel in a required dosage amount for the animal to be treated, typically about 2.5 mg/kg live weight of the animal to be treated, a polymeric species selected from the group consisting of polyvinylpyrrolidone and polyoxypropylene/polyoxyethylene block copolymers, the said polymeric species improving the bioavailability of closantel to the extend that blood plasma levels of the said compound greater than about 20 ppm over period of treatment are achievable.

20 Claims, No Drawings

LONG ACTING PARASITICIDAL COMPOSITION CONTAINING A SALICYLANILIDE COMPOUND, A POLYMERIC SPECIES AND AT LEAST ONE OTHER ANTI-PARASITIC COMPOUND

The present patent application is a nationalization of International application No. PCT/GB03/00645, filed Feb. 12, 2003, published in English, which is based on, and claims priority from, U.K. Application No. 0204712.4, filed Feb. 28, 2002, both of which are incorporated herein by reference in their entireties.

FIELD OF THE INVENTION

This invention relates to parasiticidal compositions, especially combination products for veterinary use, based on for example an avermectin or milbemycin together with another parasiticidal agent. Such combination products exhibit efficacy across a broader spectrum of parasites than is observed with the use of a single parasiticidal agent alone.

BACKGROUND OF THE INVENTION

Warm-blooded animals are subject to attack by parasites, and man has long sought to combat such parasites afflicting domestic companion animals, farmed livestock and exotic animals, to alleviate suffering and for commercial gain. The manner of attack by the parasites, and the identification of a sensitive stage in the life cycle of the parasite, may influence greatly the choice of combating agent. Thus percutaneous treatments using topically applied preparations such as lotions, paints, creams, gels, dusting powders, "pour-ons" and dips are commonly suitable for ectoparasites, but combating endoparasites requires careful selection of the method of administration and the delivery system. Oral drenches, pastes, boluses, tablets, and granules for incorporating into feed mixes are known methods capable of being used by the animal husbandrymen, but other methods which are intended to avoid use of the gastrointestinal route are typically administered by qualified practitioners. Such other methods include use of aerosols, and parenteral drug compositions which are selectively prepared as solution or suspension or micronised powder formulations intended for subcutaneous, intracutaneous, and intramuscular injection according to the intended delivery regime. These last methods require special care in formulation to avoid irritation at the site of injection or possible adverse allergic or pyrogenic reactions.

Injectable formulations are typically prepared using aqueous or non-aqueous ("solvent") vehicles. The latter class may comprise physiologically tolerable alcohols, glycols, esters, a limited range of organic aromatic solvents, and vegetable oils and extracts or modified forms thereof. In selecting vehicles, the skilled worker has to consider a number of issues including, solubility of the intended active ingredient(s), the affinity of the drug to certain vehicles, whether it will affect any essential auxiliaries, pH, stability over time, viscosity, and naturally the risk of any toxic effect upon the animal to be treated. Therefore, formulation of a parasiticide is a complex task.

Traditional parasiticides include chemical agents such as the benzimidazoles, and carbamates, and plant extracts such as the pyrethroids, which tend to be used to combat ectoparasites such as ticks and mites.

The avermectins are very potent antiparasitic agents which are useful against a broad spectrum of endoparasites and ectoparasites in mammals as well as having agricultural uses against various parasites found in and on crops and soil. The basic avermectin compounds are isolated from the fermentation broth of the soil micro-organism *Streptomyces avermitilis* and these compounds are described in U.S. Pat. No. 4,310,519. Furthermore, derivatives of these basic avermectin compounds have been prepared by a variety of chemical means.

Some of the avermectin group of compounds contain a 22,23-double bond and others contain a disaccharide at the 13-position which consists of α-L-oleandrosyl-α-L-oleandrosyl group. One or both saccharide units can be removed forming a monosaccharide or an aglycone (where both saccharides are removed) as described in U.S. Pat. No. 4,206,205. The aglycone derivatives possess a hydroxy group at the 13 position which may be removed to form the 13-deoxy compound as described in the U.S. Pat. No. 4,171,314 and U.S. Pat. No. 4,173,571. Acylation of hydroxy groups on the avermectin compounds and derivatives can be carried out as described in U.S. Pat. No. 4,201,861.

The milbemycin series of compounds, disclosed in U.S. Pat. No. 3,950,360, are structurally similar to the avermectin family in that they contain the sixteen membered macrocyclic ring. However, they do not contain the disaccharide sub-unit and there are differences in the substituent groups.

Ivermectin, disclosed in U.S. Pat. No. 4,199,569, is prepared by the selective reduction of the 22, 23 double bond of the avermectin compounds. Ivermectin is a mixture of 22,23-dihydro Avermectin B1a and B1b in a ratio of at least 80:20.

Ivermectin is an especially preferred active component in pesticidal compositions, and there is extensive literature on its activity, demonstrating its efficacy against internal and external parasites, and its ability to interfere in the life cycle of certain parasites. The Merck Index (1996) cites several references including J. C. Chabala et al, J. Med. Chem. 23, 1134 (1980); J. R. Egerton et al, Brit. Vet. J. 136, 88 (1980); W. C. Campbell et al, Science 221, 823-828 (1983) to mention but a few.

Formulation of ivermectin for the purposes of delivery in a variety of presentations, e.g. as an oral drench, pour-on, parenteral formulations, granules for adding to feed, and syringeable pastes. has proved highly challenging and numerous patents have been published on its use. Ivermectin exhibits a lipophilic character but it can be solvated in aqueous systems, and various patents describe special solvent systems for use in its formulation. Thus reference may be made at least to EP 0 045 655, and EP 0 146 414 for example.

Although ivermectin is surprisingly effective, and has enjoyed a long period of commercial success, there remains a keen interest in exploiting ivermectin against a wider range of parasites and in overcoming tolerance by some parasites which demands higher amounts of ivermectin to be delivered. Taking into account the fact that a significant volume of use of ivermectin is in protecting and treating animals intended for human consumption, there are constraints on the residual amount of ivermectin in the carcass of such an animal. Therefore, high loadings of ivermectin, even if technically feasible, in a delivery system are not necessarily the optimum solution.

Combination formulations are also desirable taking account of acquired tolerance or resistance in pests to prolonged usage of other more traditional parasiticidal agents. This phenomenon is well documented, e.g. in relation to worming compositions. Synergistic effects or complementary effects of combined parasiticidal agents have been observed as a route to combating the aforesaid tolerance problem. Synergistic anthelmintic compositions are discussed in WO 94/28887, which focuses on substituted monoand bisphenols, salicylanilides, benzene sulphonamides, halogenated benzimidazoles, benzimidazoles, and benzimidazole carbamates.

The salicylanilides, tend to be effective against fungal attack, but the chemically modified derivative closantel is an effective worming agent. Closantel is described in U.S. Pat. No. 4,005,218 and in the literature, e.g. J. Guerrero et al, J. Parasitol. 68, 616, (1983); H. Van den Bossche et al, Arch. Int. Physiol. Biochim, 87, 851(1979); H. J. Kane et al, Mol. Biochem. Parasitol. 1, 347(1980).

The opportunity to combine the use of avermectins with other parasiticidal agents has been explored already. Thus one finds that skin-absorbable pour-on formulations containing triclabendazole, optionally containing an avermectin, tetramisole or levamisole have been proposed in WO 0061068. An injectable formulation containing closantel together with an avermectin or milbemycin has been proposed in WO 95/05812. Formulations of the pour-on and injectable type are discussed in WO 01/60380, which comprise use of a pyrrolidone solvent and a bridging solvent such as a xylene, optionally including a further solubility agent such as propylene glycol caprylic acids and esters or peanut oil. This special solvent system is needed to address the difficulties of formulating differing parasiticidal agents such as closantel and ivermectin together.

Salicylanilide derivatives such as closantel provide useful control over a range of parasites and are especially useful against liver fluke. The avermectin group of anti-parasitic compounds of which ivermectin is the best known example, provide complementary protection against many other parasites such as roundworms. Therefore, there are advantages to be gained if a combination of these drugs could be provided in a form that can be conveniently administered to livestock and which will provide effective control of parasitic infection.

For ivermectin and closantel the established dose rate for injection of livestock is of the order of 200 µg/kg (ivermectin) and 2.5 mg/kg (closantel). Provision of a satisfactory aqueous formulation is problematical because the optimum pH for each drug is different. An acidic system providing the optimum pH for ivermectin, whereas closantel requires an alkaline medium for satisfactory dissolution.

Accordingly non-aqueous or essentially non-aqueous formulations were investigated. Ivermectin can be prepared in non-aqueous or low water content systems that are suitable for injection. Glycerol formal, propylene glycol, polyethylene glycol, pyrrolidone, and related solvents have been used in various formulations, singly or in combination. Patent publication WO 95/05812 discloses closantel and ivermectin solutions for injection using some of the solvents established as suitable for ivermectin (glycerol formal, polyethylene glycol, propylene glycol and water). However the effectiveness of the formulations, in terms of bioavailability of the active parasiticidal agents, described in that patent application were not disclosed.

The results of our research into the efficacy of such formulations are summarised in Table 1 presented hereinbelow.

In order to evaluate formulations of the type described in the reference WO 95/05812, administration of an ivermectin/closantel combination product as disclosed therein, at a dosage corresponding to 2.5 mg/kg closantel was carried out according to established industry practices. However, this failed to produce blood plasma levels of closantel greater than 20 ppm (Examples 1 and 2 in Table 1 reported hereinafter). According to typical experience, it was anticipated that a higher amount of closantel would have a favourable effect on the blood plasma levels. Increasing the closantel concentration in such formulations was readily achieved, allowing higher dosing of closantel in the combination product. Despite these attempts at higher dosing, administration of closantel at 5 mg/kg did not increase blood plasma levels at all and even at the exceptionally high dosing level of 7.5 mg/kg the blood plasma levels only increased to 31 ppm (Examples 3 and 4 in Table 1). Therefore the proposed formulations available from following the teachings of the reference WO 95/05812 surprisingly failed to deliver the expected solution to the problem of obtaining a satisfactory combination product.

OBJECTS OF THE INVENTION

Accordingly, it is an object of the present invention to provide improved veterinary pharmaceutical preparations. In particular it is an object of the invention to provide a composition having activity against a broad range of endo- and ectoparasites including flukes. It is a further object of this invention to provide preparations which are suitable for administration by injection. A still further object of the invention is to provide a veterinary pharmaceutical product combining ivermectin and closantel in an effective formulation enabling enhanced bioavailability of closantel in excess of the observed prior art levels.

SUMMARY OF THE INVENTION

Surprisingly it has been found that the inclusion of a significant amount of a polymeric moiety, especially polyvinylpyrrolidone (PVP) has a dramatic effect on the bioavailability of salicylanilides such as closantel in parasiticidal formulations. Lutrol, (a polyoxypropylene/polyoxyethylene block copolymer, known as a polymeric surfactant) also showed some benefit in this respect but not as demonstrably effective as the PVP.

Accordingly, the invention enables the provision of injectable parasiticidal compositions, especially combination products, based on for example an avermectin or milbemycin together with another parasiticidal agent of the salicylanilide type with effective bioavailability of the parasiticidal agents.

Thus according to one aspect of the invention, a parasiticidal composition comprises a first parasiticidal agent selected from amongst the avermectins and the milbemycins, together with another parasiticidal agent selected from the salicylanilides, in a physiologically tolerable solvent system rendering the said composition suitable for injection, characterised in that the composition comprises an amount of a polymeric species that is effective to provide blood plasma levels of the salicylanilide parasiticidal agent greater than about 20 ppm, over a period of treatment.

Preferably, the polymeric species is selected from a polyvinylpyrrolidone (PVP) or a polyoxypropylene/polyoxyethylene block copolymer, the former being especially preferred.

Polyvinylpyrrolidone is available in powder form of various molecular weights ($M_W$ circa 10,000 up to 55,000, and above: Aldrich Catalogue 2000-2001) for pharmaceutical use and is generally adopted as a dispersing and suspending agent (Merck Index). Thus it is surprising that it offers the observed beneficial effect for two reasons. Firstly, its normal use is in preparing the formulation, but here it is unnecessary, because the actives are readily introduced to the solvent system without such an aid, indeed our findings in this respect bear out the findings of the earlier patent applicant (Phoenix—W 01/60380) in terms of making a stable formulation. Secondly, a person experienced in this art would predict that macromolecules may have an adverse effect on bioavailability when present in a preparation due to interaction between the macromolecule and the drug component, leading to the so-called "drug binding" impairing bioavailability.

Therefore, hitherto on the basis of the present state of the art, prior to the present work, it could not have predicted that PVP would have a beneficial effect with respect to inhibiting depletion of effective amounts of closantel from blood after the dose is administered. Thus PVP is surprisingly found to be effective in the manufacture of a parasiticidal composition comprising closantel having long acting efficacy, such that the amount of PVP used enables the desired period of efficacy to be designed into the formulation to provide a controllable period of effective treatment whilst still permitting slaughter for human consumption of the treated animal if required having regard to the legally prescribed withdrawal period.

A suitable solvent system comprises glycerol formal (GF), or a mixture of propylene glycol (PG) and GF, or a mixture of a polyethylene glycol (PEG) and GF. A range of PEG solvents according to molecular weight is commercially available, and any of those, or others that may yet be made available, may be chosen for convenience provided that the PEG is presented or rendered available as a liquid during formulation. Typically, PEG 200 to 1500 are readily to hand from commercial sources, and thus can be used for the purposes herein, but PEG 200 to PEG 600 are usefully employed in this invention. A preferred solvent system consists of PEG 200 with GF.

Thus according to the invention, it is now possible to obtain in a single injectable formulation, an avermectin, preferably ivermectin, and a salicylanilide, preferably closantel, which is effective to deliver closantel when administered to an animal such that an effective plasma concentration of closantel is readily achieved.

The potential ranges of the preferred parasiticidal agents useful in such formulations are:

Ivermectin—from 0.1 to 10% w/v, preferably 1 to 5% w/v;
Closantel—from 1 to 30% w/v, preferably 1 to 15% w/v.

The quantity of polymeric species, especially polyvinylpyrrolidone, required to be effective depends on the desired salicylanilide activity of the mixture but typically at least 11% PVP is required to permit the higher effective amounts of e.g. closantel desired to be achieved, and good results are demonstrated at levels of 15% or more. With regard to relative ratio of polymeric component to closantel, it has been demonstrated that good bioavailability of closantel is achieved when a ratio of greater than 1.44:1 is established in the formulation.

MODES FOR CARRYING OUT THE INVENTION

Formulation Examples—Solvent Systems

A: In the preparation of a 0.5% w/v ivermectin parenteral solution the composition was as follows:

| | |
|---|---|
| Ivermectin | 0.5% w/v |
| Closantel (as Na salt) | 12.5% w/v |
| PVP (K12) | 18.0% w/v |
| Glycerol Formal | q.s. ad 100% v/v |

B: In the preparation of a 0.5% w/v ivermectin parenteral solution the composition was as follows:

| | |
|---|---|
| Ivermectin | 0.5% w/v |
| Closantel (as Na salt) | 12.5% w/v |
| PVP (K12) | 18.0% w/v |
| Propylene Glycol | 40% w/v |
| Glycerol Formal | q.s. ad 100% v/v |

C: In the preparation of a 0.5% w/v ivermectin parenteral solution the composition was as follows:

| | |
|---|---|
| Ivermectin | 0.5% w/v |
| Closantel (as Na salt) | 12.5% w/v |
| PVP (K12) | 18.0% w/v |
| Polyethylene Glycol 200 | 40% w/v |
| Glycerol Formal | q.s. ad 100% v/v |

General Method of Formulation

These formulations were made up following usual industry practice. Thus PVP is initially dissolved in the PEG 200 and half the volume of glycerol formal. Then the closantel is introduced with stirring as required. Finally the ivermectin is added, and dissolved, and the remainder of the solvent is added to the final desired volume. The solution is sterilised by membrane filtration and packaged aseptically.

Test Results:

Performance Examples 1 to 7 describe the trials of prior art proposals in comparison with formulations according to the invention.

TEST EXAMPLE 1

2.5 mg/kg closantel in a formulation of 0.5% ivermectin in glycerol formal.

TEST EXAMPLE 2

2.5 mg/kg closantel in a formulation of 0.5% ivermectin in glycerol formal and polyethylene glycol 200.

TEST EXAMPLE 3

5 mg/kg closantel in a formulation of 0.5% ivermectin in glycerol formal with polyethylene glycol 200.

TEST EXAMPLE 4

7.5 mg/kg closantel in a formulation of 0.5% ivermectin in glycerol formal with polyethylene glycol 200.

TEST EXAMPLE 5

5 mg/kg closantel in a formulation of 0.5% ivermectin in glycerol formal, and containing PVP.

TEST EXAMPLE 6

5 mg/kg closantel in a formulation of 0.5% ivermectin in glycerol formal with propylene glycol, and containing PVP.

EXAMPLE 7

5 mg/kg closantel in a formulation of 0.5% ivermectin in glycerol formal with polyethylene glycol 200, and containing PVP.

The results of bioavailability with respect to closantel are presented in the Table 1 hereinafter.

TABLE 1

| Example | Solvent System | Ivermectin Content (% w/v) | Closantel Content (% w/v) | PVP Content (% w/v) | Closantel Dose (mg/kg) | Closantel Maximum Plasma level (ppm) |
|---|---|---|---|---|---|---|
| 1 | GF | 0.5 | 6.25 | — | 2.5 | 14.8 |
| 2 | PEG/GF | 0.5 | 6.25 | — | 2.5 | 19.3 |
| 3 | PEG/GF | 0.5 | 25 | — | 5 | 18.6 |
| 4 | PEG/GF | 0.5 | 18.75 | — | 7.5 | 31.3 |
| 5 | GF | 0.5 | 12.5 | 18 | 5 | 52.8 |
| 6 | PG/GF | 0.5 | 12.5 | 18 | 5 | 48.3 |
| 7 | PEG/GF | 0.5 | 12.5 | 18 | 5 | 57.8 |

GF = Glycerol Formal
PEG = Polyethylene Glycol
PG = Propylene Glycol
In formulations using two solvents the first mentioned solvent is added at 40% With the second added to make up the required volume.

INDUSTRIAL APPLICABILITY

In view of the aforesaid advantages and properties of the compositions described herein, the invention will be usefully applied in the field of veterinary medicine in particular for combating endoparasites and ectoparasites typically afflicting livestock such as bovines, equines, ovines and caprines.

The invention claimed is:

1. A method of increasing the bioavailability of a salicylanilide anti-parasitic compound in livestock animals comprising:
   providing a concentration of the salicylanilide anti-parasitic compound to the blood or blood plasma of an animal in excess of 20 ppm,
   said providing step comprising administering by injection a solution free of precipitate, the solution comprising an effective amount of the salicylanilide anti-parasitic compound in combination with 1% to 35% w/v of a polymeric species selected from the group consisting of polyvinylpyrrolidones, and polyoxypropylene/polyoxyethylene block copolymers, an effective amount of at least one other anti-parasitic compound selected from the group consisting of avermectins and milbemycins and a physiologically acceptable solvent that does not contain either N-methylpyrrolidone or 2-pyrrolidone.

2. The method of claim 1, wherein the salicylanilide anti-parasitic compound is closantel.

3. The method of claim 2, wherein the at least one other anti-parasitic compound is ivermectin.

4. The method of claim 2, wherein the closantel is present in an amount of 1 to 30% w/v of said solution.

5. The method of claim 3, wherein the ivermectin is present in an amount of 0.1 to 10% w/v of said solution.

6. The method of claim 1, wherein the solvent is selected from the group consisting of propylene glycol, polyethylene glycol, glycerol formal, water and mixtures thereof.

7. The method of claim 1, wherein the polymeric species is a polyvinylpyrrolidone.

8. The method of claim 7, wherein the polyvinylpyrrolidone is present in an amount of at least 11% w/v of said solution.

9. The method of claim 1, wherein the salicylanilide anti-parasitic compound is administered at a dose of 5 mg/kg.

10. The method of claim 1, wherein the injection is subcutaneous injection.

11. A method of increasing the bioavailability of a salicylanilide anti-parasitic compound in livestock animals comprising:
    providing a solution free of precipitate, the solution comprising an effective amount of the salicylanilide anti-parasitic compound in combination with 1% to 35% w/v of a polymeric species selected from the group consisting of polyvinylpyrrolidones, and polyoxypropylene/polyoxyethylene block copolymers, an effective amount of at least one other anti-parasitic compound selected from the group consisting of avermectins and milbemycins and a physiologically acceptable solvent that does not contain either N-methylpyrrolidone or 2-pyrrolidone; and,
    instructing an individual to administer said solution by injection; said increasing the bioavailability of the salicylanilide anti-parasitic compound including increasing the concentration of the salicylanilide anti-parasitic compound in the blood or blood plasma in excess of 20 ppm.

12. The method of claim 11, wherein the salicylanilide anti-parasitic compound is closantel.

13. The method of claim 12, wherein the at least one other anti-parasitic compound is ivermectin.

14. The method of claim 12, wherein the closantel is present in an amount of 1 to 30% w/v of said solution.

15. The method of claim 13, wherein the ivermectin is present in an amount of 0.1 to 10% w/v of said solution.

16. The method of claim 11, wherein the solvent is selected from the group consisting of propylene glycol, polyethylene glycol, glycerol formal, water and mixtures thereof.

17. The method of claim 11, wherein the polymeric species is a polyvinylpyrrolidone.

18. The method of claim 17, wherein the polyvinylpyrrolidone is present in an amount of at least 11% w/v of said solution.

19. The method of claim 11, wherein the salicylanilide anti-parasitic compound is administered at a dose of 5 mg/kg.

20. The method of claim 11, wherein the injection is subcutaneous injection.

* * * * *